Figure 1:
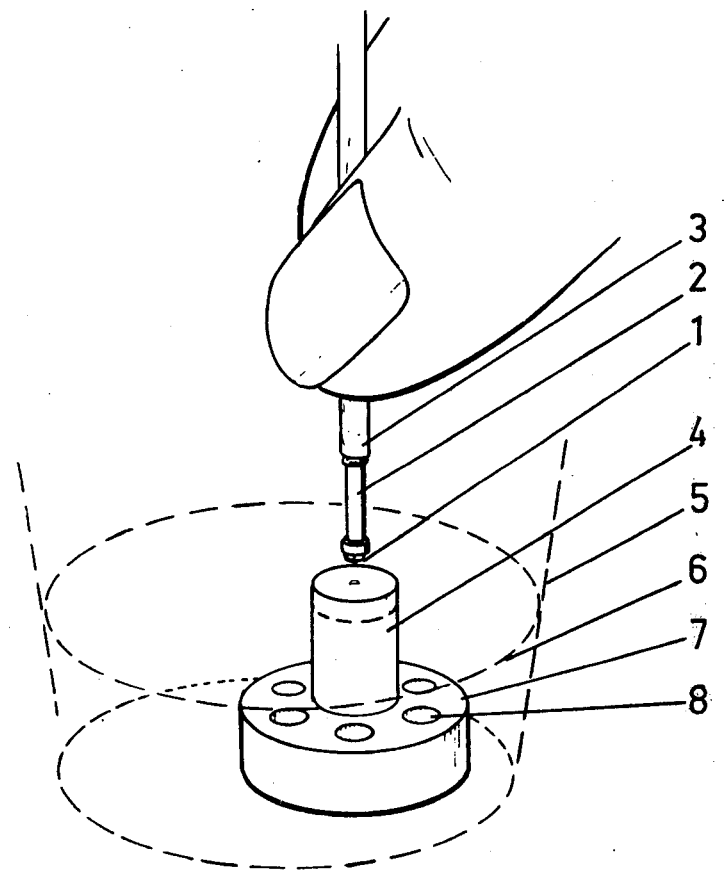

United States Patent [19]
Kindel

[11] 4,012,475
[45] Mar. 15, 1977

[54] METHOD FOR SECTIONING IN A MICROTOME AT LOW TEMPERATURE AND TRIMMING OF THE SPECIMEN TO BE SECTIONED

[75] Inventor: Erik Lennart Kindel, Bandhagen, Sweden

[73] Assignee: LKB-Produkter AB, Bromma, Sweden

[22] Filed: Aug. 23, 1974

[21] Appl. No.: 499,899

[30] Foreign Application Priority Data

Aug. 28, 1973 Sweden .............................. 7311638

[52] U.S. Cl. ............................... 264/28; 83/170; 83/915.5; 156/57; 264/330; 424/3; 427/3
[51] Int. Cl.² .......................................... B29B 3/00
[58] Field of Search ............ 83/915.5, 170; 264/28, 264/330; 427/3; 424/3; 156/57

[56] References Cited

UNITED STATES PATENTS

| | | | |
|---|---|---|---|
| 3,495,490 | 2/1970 | Dollhopf | 83/915.5 |
| 3,611,875 | 10/1971 | Wistedt | 83/915.5 |

OTHER PUBLICATIONS

"Ultra-Thin Frozen Sections for Electron Microscopy", T. C. Appleton, published by LKB Instruments, Inc. Rockville, Md., 8-1968.

*Primary Examiner*—Jeffery R. Thurlow
*Attorney, Agent, or Firm*—George H. Mitchell, Jr.

[57] ABSTRACT

According to the invention the specimen is given its desired design by pressing it towards a block, having a recess of the desired design and being cooled, preferably by liquid nitrogen.

3 Claims, 2 Drawing Figures

U.S. Patent

Mar. 15, 1977

4,012,475

METHOD FOR SECTIONING IN A MICROTOME AT LOW TEMPERATURE AND TRIMMING OF THE SPECIMEN TO BE SECTIONED

The present invention relates to a method for sectioning in a microtome at low temperature for trimming of the specimen to be sectioned, the specimen being affixed to a specimen rod.

When sectioning in a microtome it is desirable that the specimen subject to sectioning is designed in a suitable way. This is due to the fact that the sections obtained preferably should have a well defined shape. When sectioning in a microtome at room temperature the trimming could simply be achieved with good accuracy by appropriate means, such as a particular trimming device, provided with a microscope for supervision of the trimming. When sectioning work in a microtome at low temperature the specimen as well as the knife should be kept within a container, the contents of which are kept at a low temperature, for instance by liquid nitrogen. The trimming at low temperature has hitherto been accomplished manually by means of a razor blade which is introduced into the cold space followed by as rapid as possible trimming by means of said razor blade to avoid too great a temperature rise. Furthermore, the mechanical work when trimming is supplying energy to the specimen, hence raising its temperature and bringing about thermal damage. The mechanical treatment also involves risk of loosening the specimen from the specimen rod onto which it should be fixed during trimming and sectioning and there is furthermore risk of mechanical damage of the specimen.

The present invention relates to a method by means of which the design of a specimen can be accomplished at low temperature, rapidly and without disturbing heat losses.

It is known to attach a specimen, for instance in a wet state, to a specimen rod, by having the specimen stick to the specimen rod and by the latter being brought in contact with a cooled surface, for instance towards the upper surface of a metal block, which is submerged in nitrogen, or towards the top of a block of any cooled material. In the method according to the invention the cooled block then is provided with a recess of the same design as the trimmed part of the specimen should be given. By conveying the specimen possibly in a wet state, sticking to the specimen rod, towards the block, the two desired effects are achieved fairly simultaneously of trimming and fixation to the specimen rod by freezing.

The characteristics of the invention are obvious from the claims following the specification.

Figure 2:
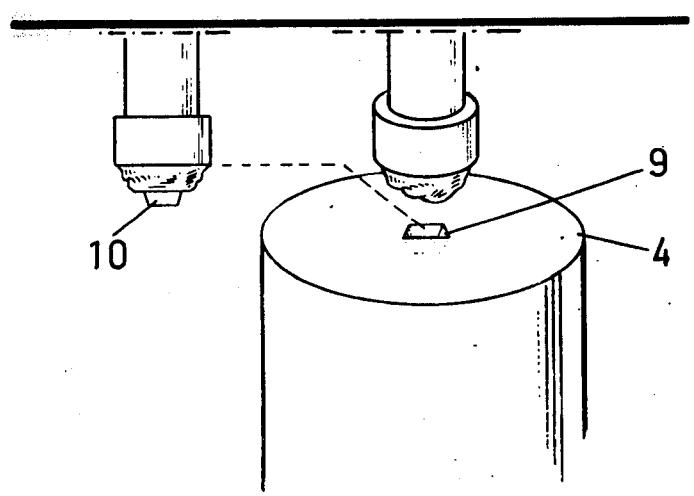

The invention will now be further described with reference to the attached drawing on which FIG. 1 shows a perspective sketch showing the method according to the invention; and FIG. 2 shows details of FIG. 1.

In FIG. 1 the number 1 denotes a specimen sticking to the specimen rod 2. The specimen rod is made of silver as an example. The specimen rod is suitably handled by an attachment 3. The number 4 denotes a block submerged into liquid nitrogen, kept within a vessel denoted by broken lines 5, in which the liquid level is denoted by 6. The block further includes a base member 7 having recesses 8 for storing of trimmed specimen being fixed to their specimen rods, respectively. In FIG. 2 the number 9 denotes the recess in the block and 10 the trimmed part of the specimen.

By the method according to the invention hence a specimen can be given the desired shape to a good accuracy rapidly and without disturbing heat losses. After trimming and fixation by pressing the specimen against the block the specimen rod with specimen can be left in one of the recesses 8 in the base member 7 after which the whole vessel rapidly can be moved to the specimen holder of the microtome. The use of a block without a base member 7 should of course fall within the scope of the invention.

I claim:

1. Method of preparing a specimen for sectioning by a microtome at low temperature comprising the steps of:
    a. bringing a specimen into contact with a rod;
    b. adhering the specimen to said rod;
    c. manipulating the rod to convey the adhered specimen into contact with a cooled block, said block being provided with a recess having the shape desired to be imparted to said specimen;
    d. and pressing at least a part of said specimen into said recess to freeze said part in said shape.

2. Method of claim 1 which includes the step of cooling said block with nitrogen.

3. Method of claim 1, which includes the step of at least partially submerging said block in liquid nitrogen.

* * * * *